(12) United States Patent
Abkowitz et al.

(10) Patent No.: US 8,741,077 B2
(45) Date of Patent: Jun. 3, 2014

(54) HOMOGENEOUS TITANIUM TUNGSTEN ALLOYS PRODUCED BY POWDER METAL TECHNOLOGY

(75) Inventors: Stanley Abkowitz, Lexington, MA (US); Susan M. Abkowitz, Burlington, MA (US); Harvey Fisher, Lexington, MA (US); Patricia J. Schwartz, Andover, MA (US)

(73) Assignee: Dynamet Technology, Inc., Burlington, MA (US)

( * ) Notice: Subject to any disclaimer, the term of this patent is extended or adjusted under 35 U.S.C. 154(b) by 0 days.

(21) Appl. No.: 13/032,374

(22) Filed: Feb. 22, 2011

(65) Prior Publication Data

US 2011/0233057 A1     Sep. 29, 2011

Related U.S. Application Data

(63) Continuation of application No. 11/705,593, filed on Feb. 13, 2007, now abandoned.

(60) Provisional application No. 60/772,896, filed on Feb. 14, 2006.

(51) Int. Cl.
| | |
|---|---|
| C22C 14/00 | (2006.01) |
| B22F 3/20 | (2006.01) |
| B22F 3/24 | (2006.01) |
| B22F 3/15 | (2006.01) |
| B22F 3/12 | (2006.01) |
| B22F 3/17 | (2006.01) |
| B22F 3/18 | (2006.01) |
| F01D 5/28 | (2006.01) |
| C23C 14/14 | (2006.01) |

(52) U.S. Cl.
USPC .......... 148/421; 420/417; 416/241 R; 419/28; 204/298.13

(58) Field of Classification Search
USPC ............... 420/430, 417; 148/421; 419/28; 416/241 R; 204/298.13
See application file for complete search history.

(56) References Cited

U.S. PATENT DOCUMENTS

| | | | | |
|---|---|---|---|---|
| 3,156,590 | A * | 11/1964 | Vordahl | 148/671 |
| 4,894,090 | A * | 1/1990 | Ekemar et al. | 75/252 |
| 5,306,569 | A * | 4/1994 | Hiraki | 428/569 |
| 5,498,302 | A * | 3/1996 | Davidson | 148/317 |
| 5,545,248 | A * | 8/1996 | Tokumoto et al. | 75/238 |
| 6,009,728 | A * | 1/2000 | Kashiwagi et al. | 65/374.11 |
| 6,279,443 | B1 * | 8/2001 | Nakahara et al. | 83/663 |
| 2005/0234561 | A1 * | 10/2005 | Nutt et al. | 623/23.53 |

FOREIGN PATENT DOCUMENTS

EP        0520465    * 12/1992    ............. C22C 29/16

OTHER PUBLICATIONS

R. Constantin and B. Miremad, "Performance of hard coatings, made by balanced and unbalanced magnetron sputtering, for decorative application", Surface Coating Technology, vol. 120-121, pp. 728-733, 1999.*

* cited by examiner

*Primary Examiner* — Jessee Roe
(74) *Attorney, Agent, or Firm* — Finnegan, Henderson, Farabow, Garrett & Dunner, LLP

(57) ABSTRACT

Titanium-tungsten alloys are described comprising tungsten ranging from about 9% to about 20% by weight, and titanium ranging from about 91% to about 80% by weight, exhibiting a yield strength of at least 120,000 psi, and a ductility of at least 20% elongation. Methods of making the alloy, and products made with the alloys are also disclosed herein.

13 Claims, No Drawings

HOMOGENEOUS TITANIUM TUNGSTEN ALLOYS PRODUCED BY POWDER METAL TECHNOLOGY

This application is a continuation application of U.S. patent application Ser. No. 11/705,593, filed Feb. 13, 2007, now abandoned, which claims the benefit of U.S. Provisional Application No. 60/772,896, filed Feb. 14, 2006 (expired), both of which are incorporated herein by reference.

Disclosed herein are homogeneous titanium-tungsten alloys and metal matrix composites having highly desirable properties. Also disclosed are methods of making such alloys and composites, as well as products comprising such alloys and composites.

Titanium metal has typically been alloyed with other metallic elements to increase the tensile strength over the pure metal. Early commercial titanium alloying elements Fe, Mn, and Cr improved strength but drastically lowered the ductility. Good ductility is desired in the typical component both to be formable (malleable) enough to produce the final shape by metalworking and to possess sufficient fracture resistance to deformation for use in the end-use application.

With the development of the Ti-6Al-4V alloy (U.S. Pat. No. 2,906,654), which is herein incorporated by reference, the young titanium industry achieved an alloy possessing higher strength combined with good ductility. Although several later alloys were developed, such alloys achieved only incremental improvements in specific properties such as higher elevated strength, better weldability or improved fatigue strength. These alloys typically possess strength levels of 130,000-140,000 psi and ductility values of 10-14% elongation, and are typical of properties comparable to the Ti-6Al-4V alloy which remains today the "workhorse" alloy of the industry with 70% of the total titanium alloy use.

For many metal working processes such as sheet bending, cold drawing and the manufacture of foil and thin wall tubing (e.g. aircraft hydraulic tubing), even Ti-6Al-4V becomes difficult to fabricate. In this case, commercially pure (CP) titanium a low alloyed titanium (Ti-3Al-2.5V) or an extra low interstitial (ELI) grade of Ti-6Al-4V is employed. In this way the ductility is improved but at a significant sacrifice of strength.

The most ductile titanium is unalloyed commercially pure titanium. The most commonly used unalloyed grade titanium is CP titanium Grade 2. This grade is widely employed for components requiring significant deformation in fabrication. CP Grade 2 has a typical tensile strength of 67,000 psi and a yield strength of 47,000 psi with a tensile ductility of 26% elongation. This high ductility permits the material to undergo severe deformation during fabrication, unlike the higher strength alloys such as Ti-6Al-4V (at 10-14% elongation) that lack the necessary malleability. A high strength titanium alloy possessing the high ductility of commercially pure titanium has long been desired to enhance the manufacturing technology of titanium components.

Among the initial elements investigated by the industry for alloying with titanium was tungsten because the resulting product was a strong wear resistant alloy. However this heavy metal element caused severe segregation problems when incorporated in the ingot melting technology of the industry. The large difference in density between tungsten ($19.3 \text{ g/cm}^3$) and titanium ($4.51 \text{ g/cm}^3$) and the disparity between the melting points of tungsten (above 3400° C.) and titanium (below 1700° C.) results in gross inhomogeneity of the alloy composition and tungsten and likely accounts for its lack of commercialization as an alloy ingredient for titanium.

To the extent that titanium alloys containing tungsten can be produced, the processes needed to achieve a homogenous alloy requires multiple melting steps and are thus very uneconomical. To avoid the foregoing problems, there is disclosed a process of hot working and then heat treating powder metal produced Ti—W alloys that is technically and economically viable alternative for developing homogeneous Ti—W alloys and composites. The resulting alloys and composites that achieve excellent strength and ductility properties are also disclosed.

It is very difficult to produce homogenous Ti alloys containing W. W is a highly refractory metal that has a much higher melting point than that of Ti. In addition W has a much higher density than Ti. For example, W melts at 3,422° C. and has a density of $19.3 \text{ gms/cm}^3$ versus 1,680° C. and $4.51 \text{ gms/cm}^3$ for Ti. The melting and casting of alloys with such disparate melting points and densities requires that ingots be melted and then remelted several times and may require hot working before remelting to achieve a homogenous alloy.

SUMMARY OF THE INVENTION

The present disclosure describes a method of making a heat treatable titanium base alloy that possesses combinations of properties that make them highly desirable. For example, in one embodiment of the invention there is described an alloy comprising titanium and 9 to less than 20% by weight of tungsten, wherein the alloy exhibits a yield strength of at least 120,000 psi and a ductility of at least 20% elongation. Applications for these highly ductile alloys include those in which the combination of high strength with high ductility is desired. For example, these materials are advantageous for medical and dental (orthopaedic implants, stents, etc.), automotive (valves, connecting rods, spring retainers, etc.), industrial (fittings, pumps, fasteners, etc.), military (ballistic armor, ordnance components, etc.) and other applications where the combination of high strength with high ductility permits readily fabrication of high strength components.

The present disclosure is also directed to alloys comprising titanium and 9% to less than 20% by weight of tungsten, 4 to 6% Al and 3 to 4% V having an ultimate tensile strength of at least 200,000 psi and useful ductility, as defined as above a 2% elongation. Products comprising such alloys are also disclosed, as are metal matrix composites comprising titanium. For example, composites comprising titanium, 9 to less than 20% by weight of tungsten, 4 to 6% Al and 3 to 4% V and 4 to 12% of a discontinuous reinforcement chosen from TiC, $TiB_2$, TiB, and combinations thereof, with an ultimate tensile strength of at least 180,000 psi are also disclosed.

The types of alloys that are further strengthened with traditional titanium alloying elements (such as Al+V) and reinforced with TiC, $TiB_2$ and/or TiB have advantages in military, medical and commercial applications where still higher strength and wear resistance is required, but ductility does not need to be as high as the previously mentioned alloys.

The desirable properties associated with the alloys and composites described herein are at least in part dependent on the ability to produce homogenous titanium-tungsten alloys. In the process described herein, homogeneity is achieved by the combination of powder metal (P/M) processing, hot working (e.g. extrusion) and subsequent heat treatment. The P/M process involves combining the tungsten and titanium powder by blending at room temperature, compacting, followed by vacuum sintering and then hot isostatic pressing to produce a fully dense material.

The PIM product is then subject to hot working followed by a heat-treatment designed to develop the desired properties. In certain embodiments, TiC, TiB$_2$ or TiB ceramic particles or combinations of such particles, can be added to these alloys to produce wear resistant high strength metal matrix composites. The method of incorporating TiC, TiB$_2$, or TiB ceramic particles in certain alloys is described in U.S. Pat. Nos. 4,731,115 and 4,968,348, which are herein incorporated by reference.

In one embodiment, the present disclosure describes an alloy comprising titanium and tungsten in an amount ranging from 9% to less than 20% by weight, such as 10% to 19%, or even 15% by weight of tungsten. Applicants have discovered that it is possible to produce such homogeneous Ti—W alloys having a yield strength of at least 120,000 psi and a ductility of at least 20% elongation.

In another embodiment, the present disclosure is directed to an alloy comprising titanium and 9% to less than 20% by weight of tungsten, 4 to 6% Al and 3 to 4% V. Such alloys have been shown to exhibit an extremely high ultimate tensile strength, such as at least 200,000 psi, and a useful ductility, which is defined herein as an elongation of up to 10% such as from 1-5%.

In yet another embodiment there is disclosed a metal matrix composite comprising a discontinuous reinforcement phase. For example, there is disclosed a metal matrix composite comprising titanium, 9 to less than 20% by weight of tungsten, 4 to 6% Al and 3 to 4% V, and 4 to 12% of a discontinuous reinforcement chosen from TiC, TiB$_2$, or TiB particles, and combinations of such particles. It has been found that such composites can exhibit an ultimate tensile strength of at least 180,000 psi.

Products comprising the previously mentioned alloys or composites are also disclosed. For example, such products may comprise a titanium material comprising 9% to less than 20% by weight of tungsten, and having a yield strength of at least 120,000 psi and a ductility of at least 20% elongation.

In another embodiment, such a product may comprise titanium and 9 to less than 20% by weight of tungsten, 4 to 6% Al and 3 to 4% V having an ultimate tensile strength of at least 200,000 psi and useful ductility of above 2% elongation.

In yet another embodiment, the product may comprise a metal matrix composite comprising a discontinuous reinforcement phase. For example, such a product may comprise a metal matrix composite comprising titanium, 9 to less than 20% by weight of tungsten, 4 to 6% Al and 3 to 4% V and 4 to 12% of a discontinuous reinforcement chosen from TIC, TiB$_2$, TiB, and combinations thereof.

Products according to the present invention include those where traditional titanium or titanium alloys may be used. These include applications that require high strength, high temperature stability, a high or useful ductility or any other applications in which anyone of such properties is desired.

For example, products according to the present invention include, medical devices, such as those chosen from orthopedic, dental, and intravascular devices. In one embodiment, orthopedic devices include knee, hip and spinal implants, intravascular devices include stents, catheters, and embolic filters, and dental devices include orthodontic implants.

Other products that may be made from the disclosed alloys and composites include:
  automotive components, such as valves, connecting rods, piston pins and spring retainers;
  military vehicle components, such as tank track, suspension, and undercarriage parts;
  tool or die materials for metal casting, such as shot sleeves, plungers and dies;
  aircraft components, such as a turbine rotor, and a leading edge of a helicopter rotor blade; and starting stock, e.g. an ingot or a billet, for subsequent processing including but not limited to casting, forging extrusion or machining.

Also disclosed herein are powder metallurgy methods of producing the alloys and composites described herein. For example, in one embodiment there is disclosed a method of making a tungsten comprising titanium material, the method comprising:
  blending a titanium containing powder with a tungsten containing powder to form a blended powder, the blended powder comprising tungsten powder in an amount ranging from 9% to less than 20% by weight of the titanium material;
  compacting the blended powder;
  consolidating the compacted and blended powder to at least 95% density by one or more processes chosen from pressing, sintering and hot isostatic pressing;
  hot working the material by a process selected from forging, rolling, extruding and spin forming; and
  heat treating the hot worked material under conditions appropriate for forming a tungsten containing titanium material having a yield strength of at least 120,000 psi and a ductility of at least 20% elongation.

The heat treating of the hot worked material comprises heating at 1450° F. for up to 4 hours to develop desired properties, such as a yield strength of at least 120,000 psi and a ductility of at least 20% elongation.

In another embodiment there is disclosed a method of making a tungsten comprising titanium material, the method comprising:
  blending a titanium containing powder with tungsten, Al and V containing powders to form a blended powder, the blended powder comprising 9 to less than 20% by weight of tungsten, 4 to 6% Al and 3 to 4% V;
  compacting the blended powder;
  consolidating the compacted and blended powder to at least 95% density by one or more processes chosen from pressing, sintering and hot isostatic pressing;
  hot working the material by a process selected from forging, rolling, extruding and spin forming; and
  heat treating the hot worked material under conditions appropriate to form a tungsten containing titanium material having an ultimate tensile strength of at least 200,000 psi and with useful elongation.

In this embodiment, the heat treating of the hot worked material comprises heating at 2100° F. for up to 24 hours to develop an ultimate tensile strength of at least 200,000 psi and having a ductility of at least 2% elongation.

In another embodiment, there is disclosed a method of making a metal matrix composite, that comprises a tungsten containing titanium material, the method comprising:
  blending a titanium containing powder with tungsten, Al, V and ceramic powders to form a blended powder, the blended powder comprising tungsten powder in an amount ranging from 9 to less than 20% by weight of tungsten, 4 to 6% Al and 3 to 4% V, and 4 to 12% of a discontinuous reinforcement chosen from TiC, TiB$_2$, or TiB, particles on combinations of such particles.
  compacting the blended powder;
  consolidating the compacted and blended powder to at least 95% density by one or more processes chosen from pressing, sintering and hot isostatic pressing;
  hot working the material by a process selected from forging, rolling, extruding and spin forming.
  heat treating the hot worked material under conditions sufficient to form a tungsten containing titanium material having an ultimate tensile strength of at least 180,000 psi.

In this embodiment, heat treating of the hot worked material comprises heating at 1450° F. for 4 hours cooling and then heating at 950° F. for 4 hours to develop an ultimate tensile strength of at least 180,000 psi.

In one embodiment, the added tungsten is in the form of a nanopowder, which is defined as a powder having a particle size from 8 angstroms to less than 3 μm, such as from 1 nm to 100 nm. Applicants have discovered that W nanopowder facilitates homogenization during subsequent processing. In accordance with the present disclosure, W nanopowder can be blended with CP (commercially pure) Ti powder and, in the case of an alloy, blended with Ti powder, other elemental powders or with master alloy powders, which is defined as the mixture of starting metal powders used to form the resulting alloy by the previously described powder metallurgy process.

All amounts, percentages, and ranges expressed herein are approximate.

The present invention is further illuminated by the following non-limiting example, which is intended to be purely exemplary of the invention.

EXAMPLES

Example 1

Ti-15% W

A powder metallurgy (P/M) technique was used to produce a Ti-15% W alloy. The P/M process involved combining the tungsten and titanium powder by blending a titanium containing powder with a tungsten containing powder to form a blended powder comprising 15% by weight of tungsten powder. The blended powder was compacted by Cold Isostatic Pressed (CIP) at 379 MPa (55 ksi), to a density of approximately 85%. The compact was then consolidated to about 95% density by vacuum sintering at 1200° C. (2250° F.) for 150 minutes to a closed porosity ranging from 94-96% density. Next, the nearly dense material was subjected to hot isostatic pressing (HIP) at 899° C. (1650° F.) for 2 hours in argon gas at a pressure of 103 MPa (15 ksi), which produced the fully dense material.

The consolidated material was next hot worked by extrusion. The hot worked material was next subjected to a heat treatment at 1450° F. for 4 hours to develop the final product having the properties shown in Table 1.

The tensile properties achieved with a heat-treated Ti-15% W alloy are compared in Table 1 with the typical and minimum specified properties of Ti-6Al-4V alloy and titanium CP titanium grade 2.

TABLE 1

| | Ultimate Tensile Strength (psi) | Yield Strength (psi) | Elongation (%) | Reduction in Area (%) |
| --- | --- | --- | --- | --- |
| Ti—6Al—4V (annealed) Typical | 135,000 | 125,000 | 14 | 25 |
| Ti—6Al—4V (annealed) Minimum | 130,000 | 120,000 | 10 | 20 |
| CP Grade 2 (Typical) | 60,000 | 50,000 | 25 | 35 |
| Ti—15W (Inventive) | 132,000 | 124,000 | 26.8 | 58.5 |

As shown in Table 1, a Ti-15W alloy made according to the disclosed process achieved a higher ductility than commercially pure titanium with strength equivalent to a Ti-6Al-4V alloy. This combination of strength with ductility makes this alloy attractive for a wide range of products requiring excellent fracture toughness, such as for dental implants.

Example 2

Ti-6Al-4V with an Addition of 15% W

A Ti-6Al-4V with an addition of 15% W was produced according to the following process. A titanium containing powder was blended with tungsten, Al and V containing powders to form a blended powder. The blended powder contained 15% by weight of tungsten, 4 to 6% Al and 3 to 4% V. The blended powder was compacted and consolidated to full density by the process described in Example 1.

The consolidated material was next hot worked by extrusion. The hot worked material was next subjected to a heat treatment at 2100° F. for 24 hours to develop the final product having the properties shown in Table 2.

TABLE 2

| | Ultimate Tensile Strength (psi) | Yield Strength (psi) | Elongation (%) | Reduction in Area (%) |
| --- | --- | --- | --- | --- |
| Ti—15W—5.2Al—3.5V Alloy | 212,100 | 196,000 | 5 | 24 |
| Ti—3Al—8V—6Cr—4Mo—4Zr | 210,000 | 200,000 | 7 | — |

As shown in Table 2, after hot working, the Ti-6Al-4V with 15% W (Ti-15W-5.2Al-3.5V) alloy exhibited an ultimate tensile strength of 210,000 psi with useful ductility above 2%. These properties rival that of the highest strength commercially available alloy Ti-3Al-8V-6Cr-4Mo-4Zr.

Example 3

Ti-6Al-4V with an Addition of 15% W and 7.5% TiC

A hard, wear resistant alloy composite was produced by adding 7.5% TiC ceramic particles to the Ti-15W-5.2Al-3.5V described above, e.g., a Ti-6Al-4V with additions of 15% W and 7.5% TiC. The blended powder was compacted and consolidated to full density by the process described in Example 1.

The consolidated material was next hot worked by extrusion. The hot worked material was next subjected to a heat treatment at 1450° F. for 4 hours cooling and then heating at 950° F. for 4 hours to produce the final product having the properties shown in Table 3.

TABLE 3

|  | UTS (psi) | YS (psi) | EL (%) | RA (%) | Hardness Rc |
|---|---|---|---|---|---|
| Ti—15W—4.8Al—3.2V—7.5TiC | 200,500 | 188,000 | 0.8 | 7.8 | 48 |

The resulting alloy, Ti-15W-4.8Al-3.2V-7.5TiC, exhibited exceptional strength. After hot working and heat treatment this composite has an ultimate tensile strength of over 200,000 psi and a remarkably high hardness for a titanium alloy (Rc=48).

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An alloy consisting of tungsten and titanium, wherein the proportions of tungsten and titanium range from about 9%:91% by weight to about 20%:80% by weight, and elemental tungsten powder and elemental titanium powder are processed to provide the alloy with a yield strength of at least 120,000 psi and a ductility of at least 20% elongation.

2. The alloy of claim 1, wherein the tungsten is present in an amount of about 15% by weight, and the titanium is present in an amount of about 85% by weight, and the alloy has a yield strength of 124,000 psi and a ductility of 26% elongation.

3. The alloy of claim 1, wherein the mixture is heated at about 1450° F. for about 4 hours.

4. The alloy of claim 1, wherein the mixture is consolidated to at least 95% density by at least one of sintering, pressing, and hot isostatic pressing.

5. The alloy of claim 1, wherein the mixture is hot-worked by at least one of forging, rolling, extruding, and spin forming.

6. The alloy of claim 1, wherein processing includes at least of one of blending, compacting, consolidating, hot-working and heat-treating.

7. The alloy of claim 1, wherein processing includes blending, compacting, consolidating, hot-working, and heat-treating.

8. A binary titanium-tungsten alloy of tungsten ranging from about 9% to about 20% by weight of tungsten, and titanium ranging from about 91% to about 80% by weight, wherein said alloy exhibits a yield strength of at least 120,000 psi, and a ductility of at least 20% elongation.

9. The alloy of claim 8, wherein the mixture is heated at about 1450° F. for about 4 hours.

10. The alloy of claim 8, wherein the mixture is consolidated to at least 95% density by at least one of sintering, pressing, and hot isostatic pressing.

11. The alloy of claim 8, wherein the mixture is hot-worked by at least one of forging, rolling, extruding, and spin forming.

12. The alloy of claim 8, wherein processing includes at least of one of blending, compacting, consolidating, hot-working and heat-treating.

13. The alloy of claim 8, wherein processing includes blending, compacting, consolidating, hot-working, and heat-treating.

* * * * *